US012806160B2

(12) United States Patent
Kitchner et al.

(10) Patent No.: US 12,806,160 B2
(45) **Date of Patent: *Nov. 24, 2026**

(54) COMPOSITIONS AND METHODS COMPRISING SANSHOOL AS LIP INTERACTING COMPONENTS

(71) Applicant: DIET SHIELD LTD, London (GB)

(72) Inventors: Andrew Kitchner, London (GB); Denis Carr, London (GB)

(73) Assignee: DIET SHIELD LTD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,975

(22) Filed: Dec. 13, 2023

(65) Prior Publication Data

US 2024/0115526 A1 Apr. 11, 2024

Related U.S. Application Data

(63) Continuation of application No. 17/861,054, filed on Jul. 8, 2022, now Pat. No. 11,931,326, which is a continuation of application No. PCT/GB2021/050050, filed on Jan. 8, 2021.

(30) Foreign Application Priority Data

Jan. 10, 2020 (GB) .................................... 2000396
Jan. 10, 2020 (GB) .................................... 2000397

(51) Int. Cl.

| | |
|---|---|
| ***A01N 43/00*** | (2006.01) |
| ***A01N 43/46*** | (2006.01) |
| ***A61K 9/00*** | (2006.01) |
| ***A61K 31/16*** | (2006.01) |
| ***A61K 31/164*** | (2006.01) |
| ***A61K 31/165*** | (2006.01) |
| ***A61K 31/55*** | (2006.01) |
| ***A61K 47/10*** | (2017.01) |
| ***A61K 47/44*** | (2017.01) |
| ***A61P 3/04*** | (2006.01) |
| ***A61P 25/34*** | (2006.01) |

(52) U.S. Cl.

CPC .......... *A61K 31/164* (2013.01); *A61K 9/0014* (2013.01); *A61K 31/16* (2013.01); *A61K 31/165* (2013.01); *A61K 47/10* (2013.01); *A61K 47/44* (2013.01); *A61P 3/04* (2018.01); *A61P 25/34* (2018.01)

(58) Field of Classification Search

None

See application file for complete search history.

(56) References Cited

U.S. PATENT DOCUMENTS

| | | | |
|---|---|---|---|
| 8,646,461 | B2 | 2/2014 | von Borstel et al. |
| 2016/0067237 | A1 | 3/2016 | Bernstein |
| 2019/0365702 | A1 | 12/2019 | Koren |

FOREIGN PATENT DOCUMENTS

| | | | |
|---|---|---|---|
| EP | 1121927 A2 | 8/2001 | |
| JP | 2010-180165 A | 8/2010 | |
| JP | 2019-202939 A | 11/2019 | |
| KR | 10-02070391 B1 | 7/1999 | |

OTHER PUBLICATIONS

Essick, G.K., Trulsson, M. (2009). Tactile Sensation in Oral Region. In: Binder, M.D., Hirokawa, N., Windhorst, U. (eds) Encyclopedia of Neuroscience. Springer, Berlin, Heidelberg. https://doi.org/10.1007/978-3-540-29678-2_5872.*

International Search Report and Written Opinion mailed Jul. 2, 2021, directed to International Application No. PCT/GB2021/050050; 15 pages.

Huang et al., (Apr. 2019). "Spilanthol from Traditionally Used Spilanthes acmella Enhances AMPK and Ameliorates Obesity in Mice Fed High-Fat Diet", NUTRIENTS, vol. 11, No. 5; 15 pages.

Wang Li et al, "Antiobesity, Regulation of Lipid Metabolism, and Attenuation of Liver Oxidative Stress Effects of Hydroxy-[alpha]-sanshool Isolated from Zanthoxylum bungeanum on High-Fat Diet-Induced Hyperlipidemic Rats", US Aug. 27, 2019 (Aug. 27, 2019), vol. 2019, p. 1-13, retrieved from the Internet at <https://downloads.hindawi.com/journals/omcl/2019/5852494.pdf>; 14 pages.

Sateesh, M. et al. "Lip: An impressive and idealistic platform for drug delivery." Journal of Pharmacy Research, (Apr. 2011). vol. 4; issue: 4, 1060-1062.

Wester and Maiback "Regional variation in percutaneous absorption." In "Topical Absorption of Dermatological Products" edited by RL Bronbaugh and HI Maiback, Marcel Dekker, Inc. (2002) Chapter 3, pp. 33-42.

Khutoryanskiy (Mucoadhesive Materials and Drug Delivery Systems. John Wiley & Sons; Jun. 12, 2014) (Year: 2014).

* cited by examiner

*Primary Examiner* — Layla Soroush

(74) *Attorney, Agent, or Firm* — Michele V. Frank; Venable LLP

(57) ABSTRACT

Provided are compositions and methods comprising a sanshool for the treatment of obesity as part of a controlled diet regime in an individual. Also provided are compositions and methods comprising a sanshool for treatment of a smoking or vaping addiction. Suitably the compositions are applied topically to the lips of the individual in response to a habitual urge to consume food, smoke or vape as required.

21 Claims, 1 Drawing Sheet

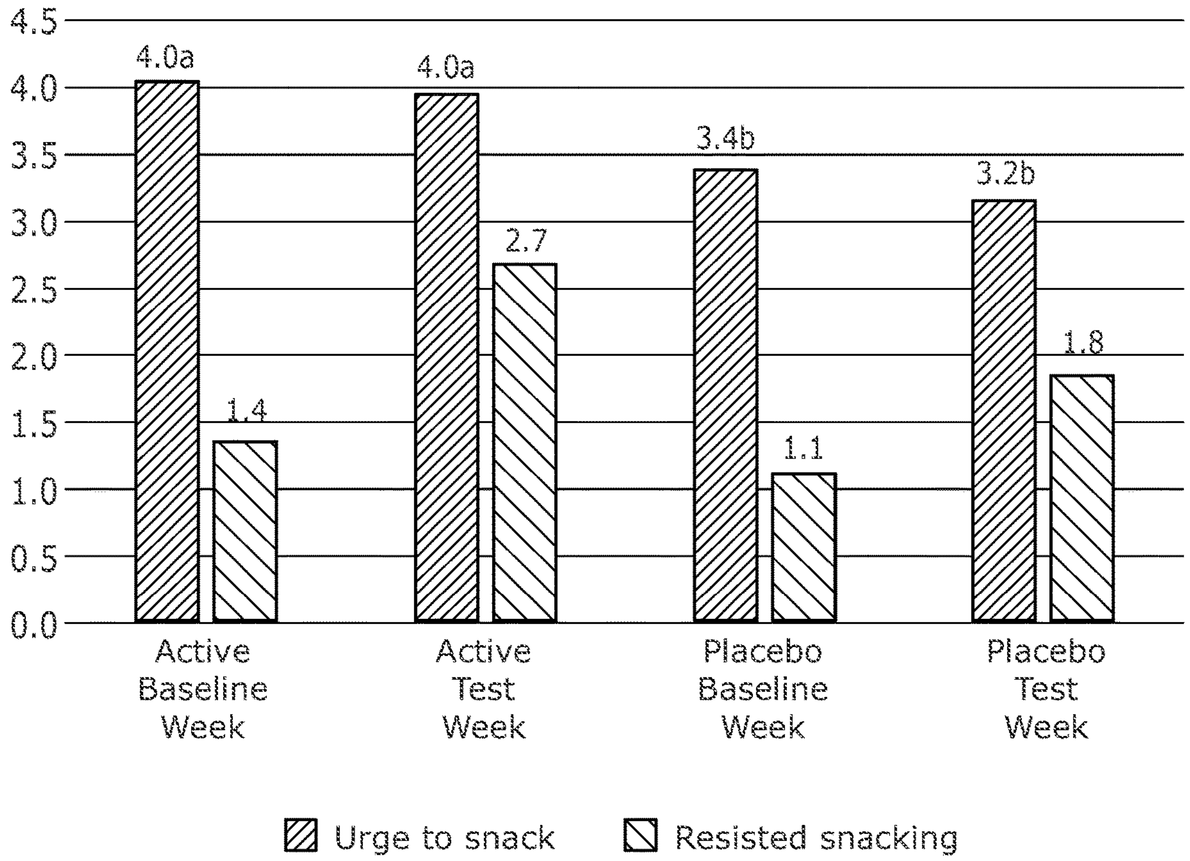
4.5
4.0
3.5
3.0
2.5
2.0
1.5
1.0
0.5
0.0
4.0a
1.4
4.0a
2.7
3.4b
1.1
3.2b
1.8
Active Baseline Week
Active Test Week
Placebo Baseline Week
Placebo Test Week
Urge to snack
Resisted snacking

COMPOSITIONS AND METHODS COMPRISING SANSHOOL AS LIP INTERACTING COMPONENTS

CROSS-REFERENCE TO RELATED APPLICATIONS

The present application is a continuation of U.S. application Ser. No. 17/861,054 filed Jul. 8, 2022, which is a continuation of International Application No. PCT/GB2021/050050, filed Jan. 8, 2021, which claims priority to United Kingdom Application Nos. 2000396.8 and 2000397.6, each filed on Jan. 10, 2020, the entire contents of each of which are hereby incorporated by reference in their entireties.

FIELD OF THE INVENTION

This invention relates to a composition comprising a lip interacting component, as well as methods and uses of the same. In particular, though not exclusively, the invention relates to the composition formulated as a lip balm, lip salve or lip stick.

BACKGROUND OF THE INVENTION

Diseases associated with lifestyle choices have become prevalent in modern urbanized society. Poor nutrition leading to obesity together with smoking or vaping contribute to the leading causes of morbidity and mortality around the world. With greater awareness and understanding of health and wellness there is a continuing need to provide products that help individuals make healthy choices and that can reinforce health positive habits.

Obesity is defined by the World Health Organisation (WHO) as an abnormal or excessive accumulation of fat, such as adipose tissue within the body. Body Mass Index (BMI) is one widely accepted measure used to define clinical obesity, with a BMI>25 considered as overweight and >30 as obese. It is estimated that nearly one billion people are clinically obese worldwide with more than double that number defined as overweight. The problems with obesity are such that according to the WHO a majority of the global population live in countries where diseases associated with being overweight kill more people than those associated with being underweight. Treating obesity and associated bariatric conditions (e.g. diabetes, heart disease, stroke, hypertension and joint replacements) represents an increasing resource burden on health providers worldwide. Obesity is also believed to be one of the leading contributors to a range of other severe diseases including cancer, dementia and is a high risk co-morbidity for respiratory infections such as COVID-19. Obesity and being overweight can further lead to low self-esteem and to myriad associated mental health issues like depression, eating disorders, anxiety, and suicidal feelings.

Various strategies have been employed in the past to help overweight people lose weight. In extreme cases surgical strategies have been used including Roux-en-Y gastric bypass surgery, Biliopancreatic diversion, Duodenal Switch and the insertion of Laparoscopic Adjustable Gastric Bands. Surgical interventions are costly and have associated dangers and health risks including infection, and because they often do not address behavioural issues they also show poor long term success.

Less invasive weight control strategies include the ingestion of substances which block the normal operation of digestive enzymes, for example preventing fat digestion.

However, in these cases, common side effects include oily rectal leakage, urgent bowel movements and gassiness. These side effects are socially embarrassing and can exacerbate any social pressure felt by the user.

Despite these various strategies, obesity and being overweight is still a prevalent world-wide health problem. There remains a need for improved solutions to the problem of helping people to manage their weight.

Key contributing factors to causing obesity and being overweight include a ready availability of energy-dense foods high in fat and sugars. Many of these foods are in the forms of snacks that make them easy to consume in between normal mealtimes. Fast foods and confectionery are often easy to resort to in societies that are increasingly urbanized and where work and life patterns have become pressured and ever more sedentary.

Snacking (e.g. unplanned calorie consumption between meals) can contribute significantly to unnecessary weight gain in a person. Snacking in particular is a problem when the person is on a managed dietary program such as a calorie controlled diet, for example the user has a daily or weekly plan in which the energy intake each day is controlled and/or substantially planned.

Consider a scenario where an average woman has a dietary target of 1500 kilocalories, typically termed "calories" (6276 kilojoules), per day in order to lose weight, whereabout 2000 calories (8368 kilojoules) are needed to maintain her weight. Similarly, an average man may be on a dietary target of 2000 calories (8368 kilojoules) to lose weight, with about 2500 calories (10,460 kilojoules) needed to maintain his weight. However, if that person consumed between their scheduled meals a glazed doughnut (e.g. about 200 calories, or 837 kilojoules), a full-fat coffee latte (e.g. about 170 calories, or 711 kilojoules), a standard size chocolate bar (e.g. about 350 calories or 1464 kilojoules), a packet of potato crisps (e.g. about 150 calories or 627 kilojoules) and an energy drink (e.g. about 130 calories or 544 kilojoules), this would significantly increase their total daily energy intake by about a further 1000 calories (4184 kilojoules). When this additional energy intake is added to the planned dietary total from their regular scheduled meals, the person would have consumed 500 calories (2092 kilojoules) beyond those needed to simply maintain their current weight. If such unplanned 'snacking' occurs regularly, without a corresponding increase in exercise or physical activity, the person will convert these excess calories into body fat. As such, their health could be detrimentally affected, and certainly their goal to lose or even simply maintain their weight will suffer.

Smoking tobacco has long been associated with a range of diseases from cancers of the lung, head and neck; cardiovascular disease; as well as birth defects in pregnant women. Despite powerful public health messaging highlighting the dangers of smoking over many decades it still represents a major cause of death in most major economies and is particularly prevalent across Asia and parts of Eastern Europe. In 2017 the annual number of recorded deaths attributed to smoking in China had almost doubled in number since 1990 to over two million. A major difficulty with tobacco smoking is that it appeals to both physical addiction to the nicotine as well as habitual addition of the ritual of repeated hand to mouth contact. Vaping has become a preferred route for many to reduce the harmful effects of inhaling tobacco smoke, but it does not reduce dependency on nicotine or break the habitual aspects of the addiction. Indeed, it has become seen as a potential gateway for children and young adults to access nicotine-based habitforming products without the stigma of tobacco use. Recent movements to decriminalise consumption of marijuana or cannabis in many countries, especially in North America, have also seen an increase in smoking or vaping of cannabinoid containing compositions for recreational purposes.

Japanese Patent Application No. 2019/202939-A describes lipsticks containing so-called angiogenic and blood circulation agents that promote visible plumping for the purpose of improving the colour of the lips. A similar cosmetic effect is sought in Korean Patent No. 10207039 B1 which utilises extract of *Zanthoxylum bungeanum* fruit (Sichuan peppercorn) to promote lip volume in a lipstick.

Hence, there exists a need for products that can address the habitual drivers that underpin poor lifestyle choices that in turn contribute to health and wellbeing problems such as obesity and smoking or vaping.

SUMMARY OF THE INVENTION

In a first aspect of the invention, there is provided a composition comprising a sanshool for use in the treatment of obesity as part of a controlled diet regime in an individual.

In a second aspect of the invention, there is provided a composition comprising a sanshool for use in treatment of a smoking or vaping addiction wherein the composition is applied to the lips of the individual in response to an urge to smoke or vape.

A third aspect of the invention provides a method for reducing a habitual urge to consume food between regular mealtimes in an individual subject, the method comprising applying a composition to the lips of an individual when the individual senses the urge to consume food, wherein the composition comprises a sanshool. In a specific embodiment of the invention, the method is a cosmetic weight loss or weight maintenance method or for cosmetic improvement of bodily appearance through managed weight loss or weight maintenance.

A fourth aspect of the invention provides a method for reducing a habitual urge to smoke or vape in an individual subject, the method comprising applying a composition to the lips of an individual when the individual senses the urge to smoke or vape, wherein the composition comprises a sanshool. In a specific embodiment of the invention, the method is a cosmetic method or for cosmetic improvement of bodily appearance through avoiding deleterious cosmetic effects associated with smoking or vaping.

A fifth aspect of the invention provides a topical composition for application to the lips of a user, the composition comprising at least a first and a second sanshool compound and a suitable excipient or carrier. Suitably the first sanshool compound is a hydroxy-alpha-sanshool and the second sanshool compound is a spilanthol.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

BRIEF DESCRIPTION OF THE DRAWINGS

One or more embodiments of the invention will now be described, by way of example only, with reference to the accompanying drawings, in which:

FIG. 1 is a graph showing use of active and placebo formulations according to one embodiment of the present invention in a trial to test resistance of the urge to consume food between mealtimes (snacking) in a cohort of overweight or obese individuals.

DETAILED DESCRIPTION OF THE INVENTION

All references cited herein are incorporated by reference in their entirety. Unless otherwise defined, all technical and scientific terms used herein have the same meaning as commonly understood by one of ordinary skill in the art to which this invention belongs.

References to 'an embodiment' disclosed herein encompasses all and any embodiments of the invention. As used in this description, the singular forms "a," "an," and "the" include plural referents unless the context clearly dictates otherwise.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "substantially" refers to the complete or nearly complete extent or degree of an action, characteristic, property, state, structure, item, or result. The exact allowable degree of deviation from absolute completeness may in some cases depend on the specific context, as would be understood to the person of skill in the art. However, in general terms the nearness of conformity to the absolute will be such as to have the same overall result—e.g. functional equivalence—as if total conformity were achieved.

References to sensations like touch may include the sensation of pressure and vice versa. References to sensations like tingling may include the sensations of fizzing, prickling, and/or pins-and-needles and vice versa. References to sensations like numbing may include the sensation of cooling and/or an analgesic effect and vice versa. References to sensations like pain may include the sensation of abrasion and vice versa.

Herein disclosed, is a composition for periodic application to the dermal layer of the lips of an individual user in the form of a lip stick, balm, salve, lotion, gloss or ointment. The composition disclosed, comprises one or more lip interacting components, that are characterised by providing one or more perceptible sensations to the user that may be selected from one or more of: heat: pain: abrasion; touch; pressure; tingling; fizzing; cooling and numbing. When the composition is applied to the lips of a user, the sensation is noticeable by the user, and can provide a sensory feedback that persists for several minutes or longer.

The invention when applied topically to the lips of a user beneficially provides a significant sensory distraction for a period of time.

As such, the compositions of the invention can be applied to the lips of a user whenever a habitual compulsion arises.

In that way, the urge to comply with the undesirable habit is arrested, subverted, ameliorated and/or prevented. This results in an increased resistance to the urge to comply, such as an increased resistance to the urge to snack unnecessarily or to smoke or vape, depending upon the context of use. Also, the composition can be formulated into a lip balm, lip salve, lip gloss or lip stick, which is convenient, simple and generally socially acceptable to use in public.

The compositions of the invention contain one or more active ingredients which act on and trigger a physiological reaction in sensory receptor cells in the lips. The interaction with the receptors in the dermal layers of the lips generates a noticeable sensation perceived by the user, e.g. heat, cold, tingling, and/or pressure etc. The sensation might even be mildly unpleasant or just unusual. Without wishing to be restricted or bound by theory, the sensation is believed to act as a sensory distraction and interrupting the habitual and psychological pathways associated with a particular urge. Additionally, or alternatively, the act of consumption of food or smoking/vaping while the sensation persists around the mouth area may be unappealing to the user. For example, drinking a carbonated energy drink might not be appealing if the user is experiencing a heightened sensory overload in the mouth area (e.g. a sensation of heat and tingling, perhaps together with a strong aroma). In addition, the mechanical act of applying a product to the lips of a user can further satisfy an instinctive psychomotor reflex in certain individuals for hand to mouth contact. This reflex may contribute to elements of habitual urge satisfaction experienced in the act of smoking/vaping and nail biting, for example.

Again, without wishing to be restricted or bound by theory, it is believed that the sensation generated in the lips provides the most beneficial distraction, but that further sensory stimulation such as aroma and flavour may add synergistically to this distraction; as does mechanically applying the lip composition. The persistence of the sensation for a period of time serves to helpfully remind the user that they are to avoiding the undesirable urge.

In an embodiment, the sensation is heat and tingling. In an embodiment, the sensation is heat and fizzing. In an embodiment, the sensation is heat and numbing. In an embodiment, the sensation is tingling and numbing. In an embodiment, the sensation is fizzing and numbing. In an embodiment, the sensation is heat, tingling and numbing. In an embodiment, the sensation is a somatosensory sensation (e.g. concerned with the conscious perception of touch, pressure, pain, temperature, position, movement and/or vibration). In an embodiment, the sensation is a paresthesia sensation (e.g. an abnormal dermal sensation such as a tingling, pricking, chilling, burning, and/or numbing sensation on the skin which is not linked to an apparent physical cause). In an embodiment, the sensation is a somatosensory and paresthesia sensation. In an embodiment, the sensation is an analgesic sensation. In an embodiment, the sensation is felt in the dermal layers of the lips. In an embodiment, the sensation is not unpleasant. In an embodiment, the sensation is mildly unpleasant.

The compositions of the invention when applied to the lips of a user beneficially provides a significant sensory distraction for a period of time.

As such, the composition of the invention can be applied to the lips of a user between meals, or whenever the user has an urge to snack. In that way, the urge to snack is arrested, subverted, ameliorated and/or prevented. This results in the consumption of fewer between meal snacks hence reduced calorific intake. This composition may be utilised as part of a planned weight loss program for obese or overweight individuals. Alternatively, the composition may be used a part of a cosmetic or healthy living weight maintenance strategy in individuals who are not clinically overweight or obese but who wish to control urges to deviate from an established nutritional pattern. This latter approach may be favoured in body conscious individuals or those working in the elite sports, fashion or entertainment sectors.

Also, the composition can be formulated for topical application to the lips, suitably in the form of a lip balm, lip salve, lip gloss or lip stick, which is convenient, simple and generally socially acceptable to use in public. The invention does not require surgical intervention (e.g. gastric band); and does not try to prevent the uptake of calories which have already been consumed (e.g. use of 'fat blocker' enzymes), and any of the potential consequential embarrassing side-effects such as rectal leakage.

The invention contains one or more ingredients which act on receptors in the lips. The interaction with the receptors in the dermal layers of the lips generates a noticeable sensation, e.g. heat, cold, tingling and/or pressure etc. The sensation might even be slightly unpleasant or just unusual. Without wishing to be restricted or bound by theory, the sensation is believed to aid the person to think of something other than snacking, e.g. to act as a sensory distraction.

In an embodiment, the sensation is perceived by the user as heat and tingling. In an embodiment, the sensation is perceived by the user as heat and fizzing. In an embodiment, the sensation is perceived by the user as heat and numbing. In an embodiment, the sensation is perceived by the user as tingling and numbing. In an embodiment, the sensation is perceived by the user as fizzing and numbing. In an embodiment, the sensation is perceived by the user as a combination of heat, tingling and numbing. In an embodiment, the sensation is a somatosensory sensation (e.g. concerned with the conscious perception of touch, pressure, pain, temperature, position, movement and/or vibration). In an embodiment, the sensation is a paresthesia sensation (e.g. an abnormal dermal sensation such as a tingling, pricking, chilling, burning, and/or numbing sensation on the skin which is not linked to an apparent physical cause). In an embodiment, the sensation is a somatosensory and paresthesia sensation. In an embodiment, the sensation is an analgesic sensation. In an embodiment, the sensation is felt in the dermal layers of the lips. In an embodiment, the sensation is not unpleasant. In an embodiment, the sensation is mildly unpleasant.

Hence, according to an embodiment of the present invention there is provided a method for treating an unwanted psychological urge to consume food, beverages or to smoke/vape in an individual in need thereof, comprising applying a composition comprising an ingredient that induces a somatosensory sensation to the lips of the individual.

According to a further embodiment of the present invention there is provided a method for treating an unwanted psychological urge to consume food, beverages or to smoke/vape in an individual in need thereof, comprising applying a composition comprising an ingredient that induces a sensation of paresthesia to the lips of the individual.

In yet a further embodiment of the present invention there is provided a method for treating an unwanted psychological urge to consume food, beverages or to smoke/vape in an individual in need thereof, comprising applying a composition comprising one or more ingredients that induce a somatosensory sensation and a sensation of paresthesia to the lips of the individual.

In an embodiment, the composition is safe to ingest in the amounts applied. In an embodiment, the composition will contain naturally sourced and/or organically sourced ingredients. In an embodiment, the ingredients will be safe for all kinds of users, such as children, breast-feeding mothers and people with the most common kinds of allergies etc.

In an embodiment, the sensation induced by the compositions is noticeable by the user for a prolonged period of time, optionally for a period of time in excess of any one of about 5, 10, 15, 20, 25, 30, 35, 40, 45, 50, 60, 120 and 180 minutes. Optionally, the period of time should be substantially shorter than the time between scheduled meals e.g. less than 12, 10, 8, 7, 6, 5 and 4 hours. Optionally, the period of time is between 5 and 60 minutes, further optionally between 10 and 40 minutes, still further optionally between 20 and 30 minutes.

This noticeable sensation (e.g. a person or a panel of testers, being able to positively confirm that the sensation is present, and preferably confirm the sensation is present for 5 seconds or more) can be used to distract the person from the impulse to snack. A panel of testers may be for example made up of from 3 to 35 adults (e.g. 3, 5, 7 or 11). The adults between the ages of 18 to 65, and each without any outstanding medical condition or illness that would affect their ability to smell and to taste and/or to perceive sensations when a composition as described herein is applied to their lips. In the situation where a panel of testers is not unanimous in their view, the majority (or average) view of the panel may be taken. In order to check that the person has a suitable sensory ability to taste or smell, each ingredient may be given to the tester as a control composition sample. For example, a control composition sample may be the same as in the Examples, but where only one active ingredient is included in the composition, but at double or triple the strength mentioned in the Examples. An alternative is where a comparison to a placebo is used, wherein the placebo composition does not contain an active ingredient.

The period of time the sensation is noticeable by the user, need only be sufficient to arrest, subvert, ameliorate and/or prevent a habitual urge. For example, a duration of five minutes may be a sufficiently long period of time to distract a user from the urge to eat or smoke/vape. However, a longer duration of action can beneficially give a longer window in which the deterring effect can operate. The selection and concentration of the active ingredients (e.g. lip interacting components) can be selected to produce a desired sensation for a suitably long noticeable period of time. For example, the prickling/tingling sensation produced by the active ingredients in Szechuan (Sichuan) pepper oil, the sanshool compounds may last up to about 40 minutes, or longer, depending on the concentration of the active ingredients. The active ingredients in hot chilli peppers, capsaicins, may produce a heat sensation that lasts from about 5 to 15 minutes. The sensation produced by Szechuan pepper oil is quite unusual, and distinctly different from the strong heat sensation usually produced by chilli peppers. Szechuan pepper oil is also less pungent than chilli peppers. As such the sensation produced in the mouth area (e.g. inclusive of the lips) by sanshool compounds present in Szechuan pepper oil is especially effective in distracting users from unwanted urges, and is more acceptable to some users who do not like the stronger heat sensation produced by chilli peppers. Similar effects may be obtained by using extracts of *Acmella oleracea* that contain spilanthol (also referred to as spilanthes extract).

In an embodiment, the composition comprises two or more of the lip interacting components. In an embodiment, the composition comprises three or more of the lip interacting components. The use of more than one lip interacting component can produce a tailored sensation profile, depending on the ingredients selected and the concentrations of each. For example, a combination of Szechuan pepper oil with eucalyptus oil may produce the unusual sensation of heat, tingling with a cooling and numbing sensation. A heat and tingling paresthesia sensation is provided by the Szechuan pepper oil and a cooling and numbing somatosensory sensation is provided by the eucalyptus oil. Relative amounts of each ingredient will produce a different overall sensation profile. Further, for example, a third ingredient such as an extract from chilli peppers that contains capsaicin could be added to give an initial strong heat sensation in the sensation profile.

In a specific embodiment of the invention, the composition comprises at least one sanshool and at least another lip sensation inducing component. Suitably the further component may comprise another sanshool compound that differs in chemical structure to the first. Optionally, the composition comprises at least a sanshool and at least a spilanthol.

In an embodiment, the composition comprises a first lip interacting component, which provides a somatosensory sensation and a second lip interacting component, which provides a paresthesia sensation. In an embodiment, the second lip interacting component has a topical analgesic (pain relief) property.

In an embodiment, the composition further comprises a flavour component with a noticeable/strong taste property (e.g. a person, or a panel of testers, being able to positively confirm that the flavour is present, and optionally able to confirm that the flavour is present for 5 seconds or more (e.g. about 5 minutes to 45 minutes, or more). In an embodiment, the flavouring is selected from one or more of astringent, bitter, pungent, sour, salty and sweet. In an embodiment, the composition further comprises a scent component with a noticeable/strong aromatic property (e.g. a person, or a panel of testers, being able to positively confirm that the aroma is present, and optionally able to confirm that the aroma is present for 5 seconds or more (e.g. about 5 minutes to 45 minutes, or more). In an embodiment, the aroma property is selected from one or more of fragrant, citrus, fruity, woody/resinous, chemical, sweet, minty/peppermint, toasted/nutty, pungent and decayed. In an embodiment, the flavour component and/or a scent component is obtained from an essential oil, such as thyme essential oil, rosemary essential oil, pine essential oil, lavender essential oil, or a citrus essential oil. In an embodiment, for example, the flavour component and/or scent component may be selected from any one of Limonene Essential Oil, Citronella Essential Oil, Orange Oil, Coffee Fragrance Oil, Freshly Cut Grass Fragrance Oil (e.g. green notes), vanilla and vanilla extract.

In an embodiment, one or more of: the first lip interacting component, scent component and flavour component are pungent (e.g. having an intense flavour or aroma). In an embodiment, one or more of: the first lip interacting component, scent component and flavour component are not unpalatable to the user. In an embodiment, one or more of: the first lip interacting component, scent component and flavour component are mildly unpalatable to the user.

These additional components added to the composition can assist in deterring the user from unwanted urges. Without wishing to be restricted or bound by theory, it is believed that this smell/taste adds to a sensory overload of the senses of the user, and so helps to deter the user from wanting to consume while the sensation persists. If the urge returns, the composition can be reapplied easily and frequently.

In an embodiment, the composition further comprises a dysgeusic component (e.g. giving a distortion of the sense of taste), which alters the perception of taste of the user. In an embodiment, the dysgeusic component is selected from one or more of: sodium lauryl ether sulphate, sodium lauryl sulfate, bromelain, miraculin and cynarine.

In an embodiment, the composition further comprises an appetite suppressant such as an over-the-counter appetite suppressant. In an embodiment, the composition further comprises a natural sourced appetite suppressant or an over-the-counter appetite suppressant such as Conjugated Linoleic Acid (CLA), Bitter Orange (Synephrine), *Garcinia cambogia, Hoodia gordonii,* Green Coffee Bean Extract, Guarana, Saffron Extract, Forskolin, and Chromium Picolinate.

In an embodiment, the composition is not formulated in/as a personal care product. In an embodiment, the composition is not formulated in/as a soap, deodorant, antiperspirant, skin lotion, skin cream, moisturizer or ointment. In an embodiment, the composition is not formulated in/as a food. In an embodiment, the composition is not formulated in/as a candy, lozenge, confectionery, chewing gum, mint, chocolate, cake, cookie, beverage, alcoholic beverage, seasoning, salad dressing or dip. In an embodiment, the composition is not formulated in/as a pharmaceutical product. In an embodiment, the composition is not formulated as a topical medicine, nebulizer, medicated lozenge or chewable medicine.

In an embodiment, the lip interacting component consists of a first lip interacting component and a second lip interacting component as defined hereinabove.

In an embodiment, the active component, or first lip interacting component, is selected from a sanshool. Suitably the sanshool is derived or extracted from a Szechuan pepper oil, or is a pungent component extracted or extractable from Szechuan peppercorns. In an embodiment, the active component, or first lip interacting component, is a pungent component extracted from the plants in the genus *Zanthoxylum,* suitably *Z. bungeanum* or *Z. armatum,* or the fruiting bodies thereof. In an embodiment, the lip interacting component, or first lip interacting component, interacts with dermal lip receptors which are the same as the receptors which interact with hydroxy-α-sanshool.

In an embodiment, the lip interacting component, or first lip interacting component, acts at the tandem pore domain potassium channels KCNK3, KCNK9 and/or KCNK18. In an embodiment, the lip interacting component, or first lip interacting component, excites sensory neurons by inhibiting two-pore potassium channels. In an embodiment, the lip interacting component, or first lip interacting component, excites neurons involving inhibition of pH- and anesthetic-sensitive two-pore potassium channels (e.g. KCNK3, KCNK9 and/or KCNK18). In an embodiment, the lip interacting component, or first lip interacting component, excites D-hair afferent nerve fibers, a subset of the sensitive light touch receptors in the skin, and/or targets populations of Aβ and C-fiber nerve fibers. Without wishing to be restricted or bound by theory, it is believed that components like hydroxy-α-sanshool (e.g. from Szechuan peppers), excite neurons through a mechanism involving inhibition of pH- and anesthetic-sensitive two-pore potassium channels (KCNK3, KCNK9 and/or KCNK18), and so will give the unusual and complex psychophysical sensations associated with Szechuan pepper oil, e.g. a tingling and buzzing sensation. Similarly, it is understood that components acting like hydroxy-α-sanshool (e.g. from Szechuan pepper), excite D-hair afferent nerve fibers, a subset of the sensitive light touch receptors in the skin, and/or targets populations of Aβ and C-fiber nerve fibers and so will give the unique and complex psychophysical sensations associated with Szechuan pepper oil. As such, other components similarly interacting with these receptors are also considered within the scope of the lip interacting component, or first lip interacting component.

In an embodiment, the active component, or first lip interacting component, is a sanshool compound, such as a hydroxy-sanshool (e.g. hydroxy-α-sanshool), or is a related compound such as spilanthol. In an embodiment, the active component, or first lip interacting component, is selected from one or more of:

TABLE 1

| S # | Sanshool name | Chemical structure |
|---|---|---|
| 1 | α-Sanshool | 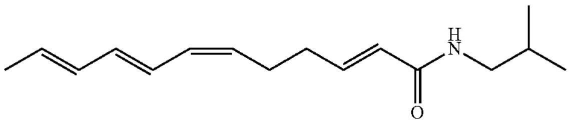 [SMILES: C/C=C/C=C/C=C\CC/C=C/C(=O)NCC(C)C] |
| 2 | β-Sanshool | 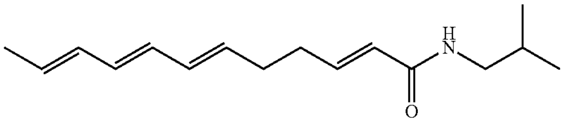 [SMILES: C/C=C/C=C/C=C/CC/C=C/C(=O)NCC(C)C] |
| 3 | γ-Sanshool | 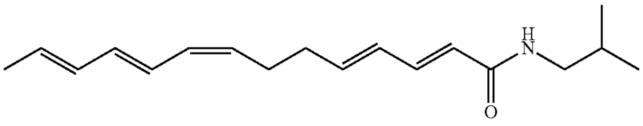 [SMILES: C/C=C/C=C/C=C\CC/C=C/C=C/C(=O)NCC(C)C] |
| 4 | δ-Sanshool | 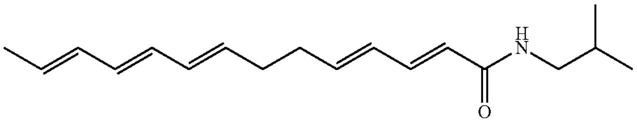 [SMILES: C/C=C/C=C/C=C/CC/C=C/C=C/C(=O)NCC(C)C] |

TABLE 1-continued
| S # | Sanshool name | Chemical structure |
|---|---|---|
| 5 | Hydroxy-α-sanshool | 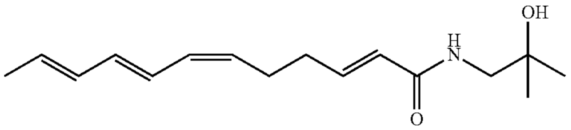 [SMILES: C/C=C/C=C/C=C\CC/C=C/C(=O)NCC(C)(C)O] |
| 6 | Dihydroxy-α-sanshool | 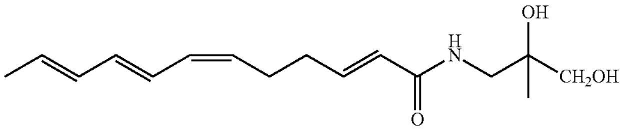 [SMILES: C/C=C/C=C/C=C\CC/C=C/C(=O)NCC(C)(O)CO] |
| 7 | Hydroxy-β-sanshool | 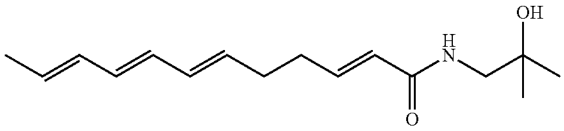 [SMILES: C/C=C/C=C/C=C/CC/C=C/C(=O)NCC(C)(C)O] |
| 8 | Dihydroxy-β-sanshool | 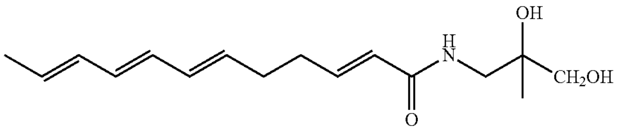 [SMILES: C/C=C/C=C/C=C/CC/C=C/C(=O)NCC(C)(O)CO] |
| 9 | Hydroxy-γ-sanshool | 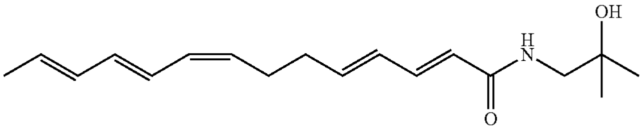 [SMILES: C/C=C/C=C/C=C\CC/C=C/C=C/C(=O)NCC(C)(C)O] |
| 10 | Hydroxy-γ-isosanshool | 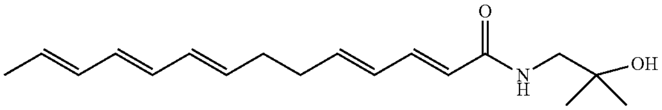 [SMILES: C/C=C/C=C/C=C/CC/C=C/C=C/C(=O)NCC(C)(C)O] |
| 11 | Hydroxy-ε-sanshool | 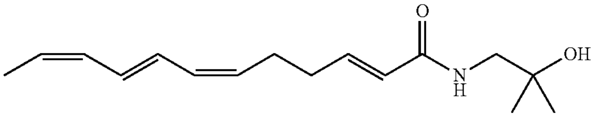 [SMILES: C\C=C/C=C/C=C\CC/C=C/C(=O)NCC(C)(C)O] |
| 12 | Hydroxy-ζ-sanshool | 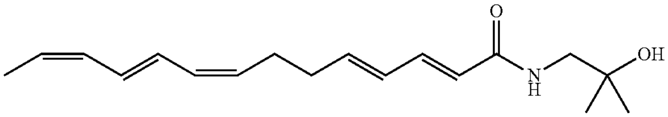 [SMILES: C\C=C/C=C/C=C\CC/C=C/C=C/C(=O)NCC(C)(C)O] |
| 13 | Bungeanool | 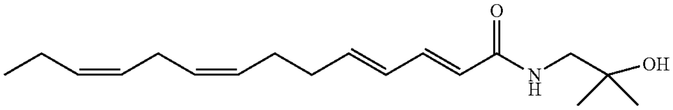 [SMILES: CC/C=C\C/C=C\CC/C=C/C=C/C(=O)NCC(C)(C)O] |
| 14 | Isobungeanool | 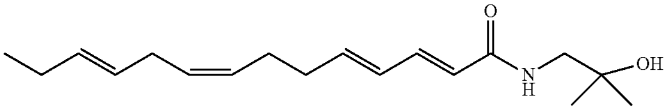 [SMILES: CC/C=C/C/C=C\CC/C=C/C=C/C(=O)NCC(C)(C)O] |
| 15 | (2E,7E,9E)-N-(2-hydroxy-2-methylpropyl)-6,11-dioxo-2,7,9-dodecatrienamide | 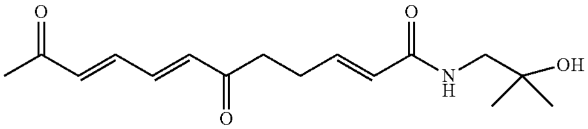 [SMILES: CC(=O)/C=C/C=C/C(=O)CC/C=C/C(=O)NCC(C)(C)O] |

TABLE 1-continued

| S # | Sanshool name | Chemical structure |
|---|---|---|
| 16 | (2E,6E,8E)-N-(2-hydroxy-2-methylpropyl)-10-oxo-2,6,8-decatrienamide | 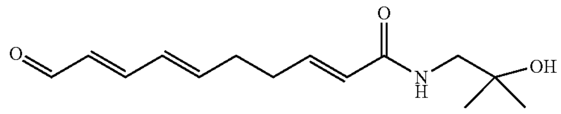 [SMILES: CC(C)(O)CNC(=O)/C=C/CC/C=C/C=C/C=O] |
| 17 | Spilanthol | 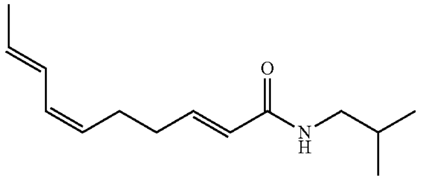 [SMILES: C/C=C/C=C\CC/C=C/C(=O)NCC(C)C] |

In an embodiment, the active component, or first lip interacting component, is selected from one or more of: α-Sanshool, β-Sanshool, γ-Sanshool, δ-Sanshool, Hydroxyl-α-sanshool, Dihydroxy-α-sanshool, Hydroxyl-β-sanshool, Dihydroxy-β-sanshool, Hydroxyl-γ-sanshool, Hydroxy-γ-isosanshool, Hydroxyl-ε-sanshool, Hydroxyl-ζ-sanshool, Bungeanool, Isobungeanool, (2E,7E,9E)-N-(2-hydroxy-2-methylpropyl)-6,11-dioxo-2,7,9-dodecatrienamide, (2E,6E,8E)-N-(2-hydroxy-2-methylpropyl)-10-oxo-2,6,8-decatrienamide and spilanthol.

In an embodiment, the lip interacting component, or first lip interacting component, is selected from one or more of:

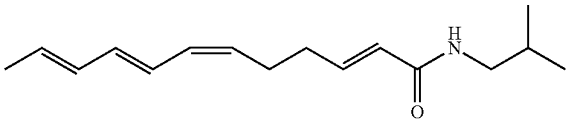

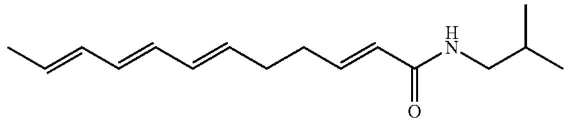

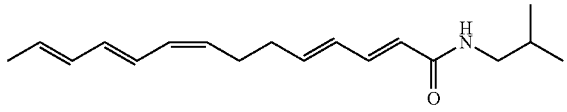

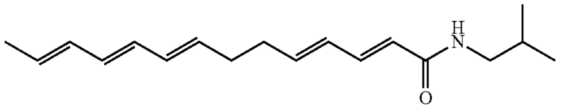

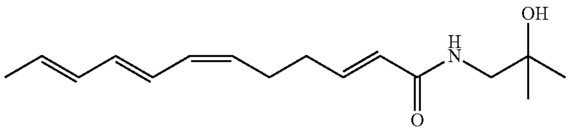

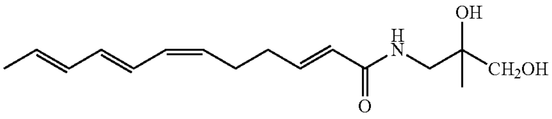

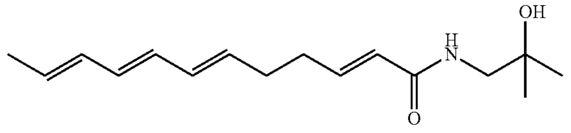

-continued

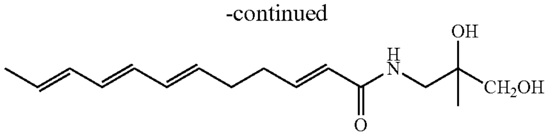

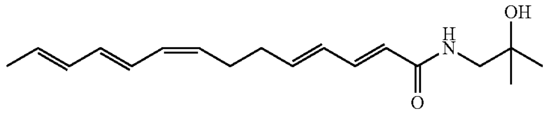

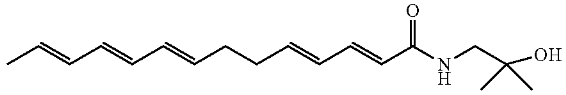

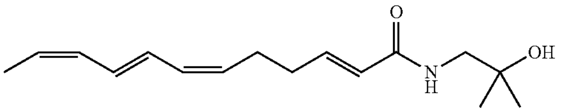

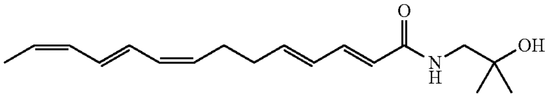

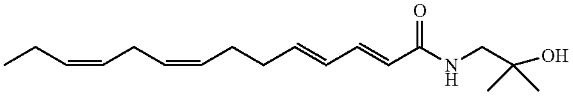

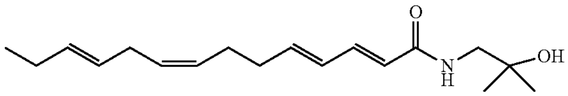

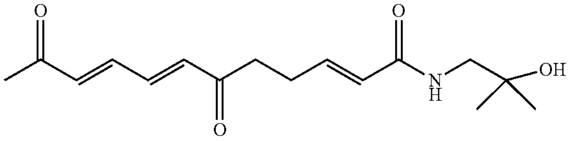

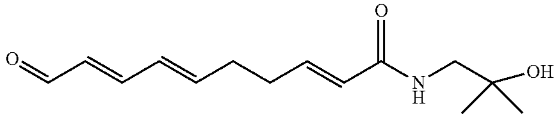

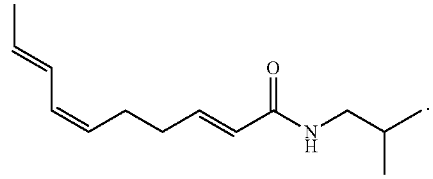

In an embodiment, the lip interacting component, or first lip interacting component, is selected from: a capsaicinoid, such as capsaicin, or a related compound, or is a pungent component extracted or extractable from chilli peppers. In an embodiment, the lip interacting component, or first lip interacting component, interacts with dermal lip receptors which are the same as the receptors which interact with capsaicin.

In an embodiment, the lip interacting component, or first lip interacting component, is an agonist at the pain-integration channels, such as TRPV1 and/or TRPA1. Without wishing to be restricted or bound by theory, it is understood that components acting like capsaicin (e.g. from chilli peppers), is an agonist at the pain-integration channels, such as TRPV1 and/or TRPA1, and so will give the heat or pain-like sensations associated with chilli peppers.

In an embodiment, the lip interacting component, or first lip interacting component, is selected from one or more of:

In an embodiment, the lip interacting component, or first lip interacting component, is selected from one or more of: Capsaicin; Dihydrocapsaicin, Nordihydrocapsaicin, Homocapsaicin, Homodihydrocapsaicin and Nonivamide.

In an embodiment, the lip interacting component, or first lip interacting component, is selected from one or more of:

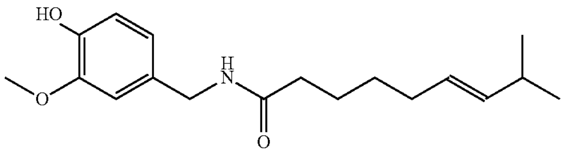

TABLE 2

| C # | Capsaicinoid name | Chemical structure |
| --- | --- | --- |
| 1 | Capsaicin | 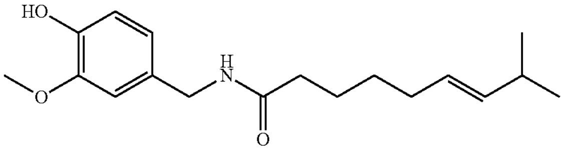 [SMILES: COc1cc(CNC(=O)CCCC/C=C/C(C)C)ccc1O] |
| 2 | Dihydrocapsaicin | 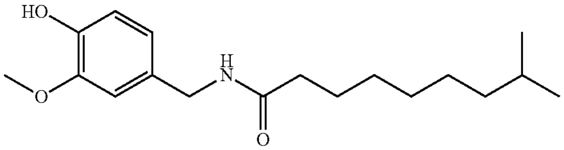 [SMILES: COc1cc(CNC(=O)CCCCCCC(C)C)ccc1O] |
| 3 | Nordihydrocapsaicin | 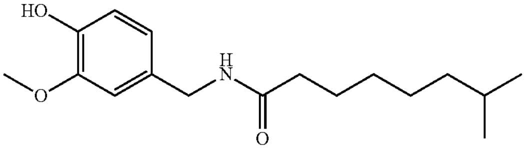 [SMILES: COc1cc(CNC(=O)CCCCCC(C)C)ccc1O] |
| 4 | Homocapsaicin | 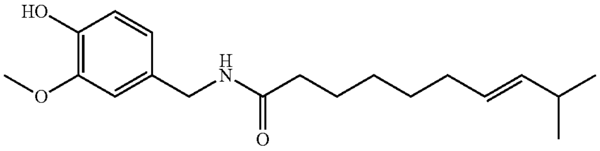 [SMILES: COc1cc(CNC(=O)CCCCC/C=C/C(C)C)ccc1O] |
| 5 | Homodihydrocapsaicin | 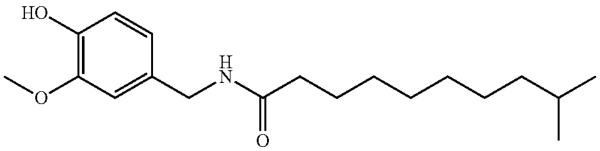 [SMILES: COc1cc(CNC(=O)CCCCCCCC(C)C)ccc1O] |
| 6 | Nonivamide | 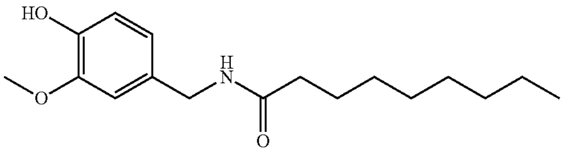 [SMILES: CCCCCCCCC(=O)NCc1ccc(O)c(OC)c1] |

-continued

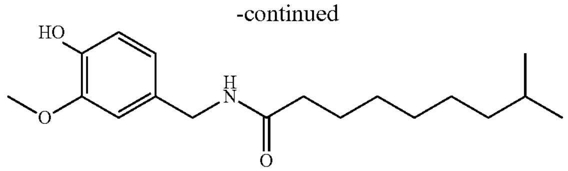

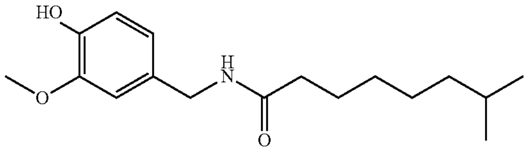

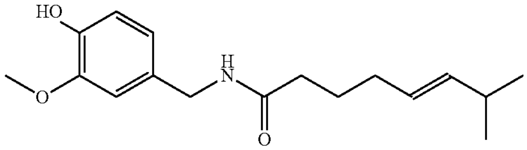

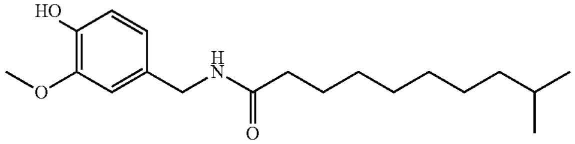

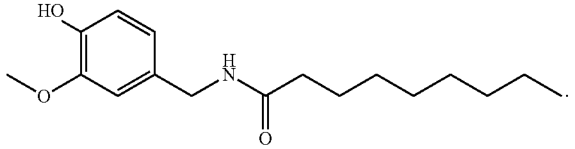

In an embodiment, the active component, or first lip interacting component, is selected from: Japanese Pepper extract, Jambu Oleoresin, Sichuan buttons, Sichuan button extract, a pungent component extracted or extractable from Sichuan buttons and Spilanthes. In an embodiment, the lip interacting component, or first lip interacting component, is selected from: black pepper extract, Chavicine and Piperine. In an embodiment, the lip interacting component, or first lip interacting component, is selected from: ginger, gingerol or ginger oleoresin. In an embodiment, the lip interacting component, or first lip interacting component, is selected from vanillin or a vanillin derived and/or related compound.

In an embodiment, the composition further comprises a compound with the formula (I)

$$F—CO—NH—R^1 \quad (I)$$

wherein, F is an alkane chain of 8 to 15 carbon atoms comprising at least one double bond, the chain may be branched or unbranched, the double bonds may be independently cis- or trans-, and wherein the carbon atoms may be substituted with one or more of O, CO, N, NH, $NH_2$, lower alkyl, lower alkyl ether and OH groups; and wherein $R^1$ may be an alkyl chain of 1 to 9 carbon atoms, the chain may be branched or unbranched, and wherein the carbon atoms may be substituted with one or more of O, CO, N, NH, $NH_2$, lower alkyl, lower alkyl ether and OH groups;

or $R^1$ may be a hydrocarbon group comprising 6 to 15 carbon atoms, of which 6 to 10 carbon atoms form an aromatic ring system, the ring system may be substituted by one or more groups selected from, O, S, N, NH, and/or the carbon atoms of the ring system may have substituents selected from OH, SH, lower alkyl group, lower alkyl ether, lower alkyl primary amine, lower alkyl secondary amine, lower alkyl ester, and wherein the lower alkyl group is a linear or branched group comprising 1 to 5 carbon atoms.

In an embodiment, F comprises 8 to 14 carbon atoms, optionally 10 to 12 carbon atoms, further optionally 9 or 11 carbon atoms. In an embodiment, F comprises 9 carbon atoms. In an embodiment, F consists of carbon and hydrogen atoms. In an embodiment, F comprises 3 to 5 carbon-carbon double bonds, optionally 4 carbon-carbon double bonds. In an embodiment, F is unbranched.

In an embodiment, $R^1$ comprises 3 to 5 carbon atoms, optionally 4 carbon atoms. In an embodiment, $R^1$ comprises 4 carbon atoms in an isobutene configuration. In an embodiment, $R^1$ consists of carbon, hydrogen and oxygen atoms. In an embodiment, $R^1$ comprises 4 carbon atoms in an isobutene configuration and substituted with one or two OH groups, optionally $R^1$ is $CH_2C(OH)(CH_3)_2$. In an embodiment, $R^1$ comprises a methoxy substituted phenol group, optionally $R^1$ is a 4-hydroxy, 2-methoxy phenyl or benzyl group.

In an embodiment, the second lip interacting component is selected from one or more of: menthol; menthone, menthyl acetate, eucalyptol, alpha-terpineol; camphor, pinene, limonene, pulegone and eugenol. In an embodiment, the second lip interacting component is extracted from or extractable from the leaves of a eucalyptus plant, leaves of peppermint, flowers of lavender or cloves. In an embodiment, the second lip interacting component acts on TRPM8 receptors. In an embodiment, the second lip interacting component, interacts with dermal lip receptors which are the same as the receptors which interact with menthol.

In an embodiment, the composition further comprises a compound comprising a Core Structure of 1-methyl, 4-isopropyl cyclohexane (i.e. p-Menthane)

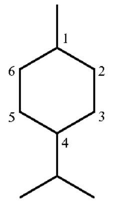

(1-methyl, 4-isopropyl cyclohexane)

wherein the Core Structure comprises one or more additional structural elements selected from:

OH group, C(O)O-(lower alkyl group), CO group, C—C double bond, O, a Linking Group linking the tertiary carbon of the isopropyl group to the 1- or 6-position of the Core Structure, wherein the Linking Group maybe a single carbon-carbon bond, or may comprise one or more groups selected from $CH_2$, CO or O; or there may be a ring-forming carbon-carbon bond linking the 2- and 4-position of the Core Structure;

and wherein the lower alkyl group is a linear or branched group comprising 1 to 5 carbon atoms;

and optionally, when present, independently:

the OH is at the 1-, 3- or 4-position of the Core Structure, or the OH is located on the tertiary carbon of the isopropyl group of the Core Structure;

the C(O)O-(lower alkyl group) is at the 3-position of the Core Structure, or the C(O)O-(lower alkyl group)

is located on the tertiary carbon of the isopropyl group of the Core Structure;

the CO is at the 2- or 3-position of the Core Structure;

the olefin is at the 1,2-position or 3,4-position of the Core Structure, or forms a double bond within the isopropyl group;

the O forms a cyclo epoxide group across the 1,2-position of the Core Structure, or forms a cyclo epoxide from the 4-position to a primary carbon of the isopropyl group of the Core Structure; or forms a furan structure bonding from the 3-position to a primary carbon of the isopropyl group of the Core Structure;

the Linking Group is an O group and bridges to the 1-position of the Core Structure; or the Linking Group is a carbon-carbon single bond and bridges to the 6-position of the Core Structure;

the ring-forming carbon-carbon bond links the 2- and 4-position of the Core Structure when the 1-methyl group of the Core Structure is unsaturated.

the OH is at the 3-position of the Core Structure.

In an embodiment, the composition comprises one or more of:

TABLE 3

| T # | Compound name | Chemical structure |
|---|---|---|
| 1 | Menthol | 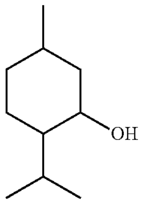 |
| 2 | Eucalyptol | 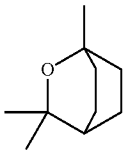 |
| 3 a-d | Terpineols (e.g. α, β, γ and 4-) | 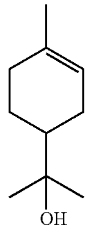 α 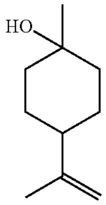 β 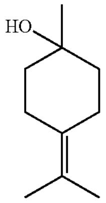 γ 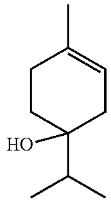 4- |
| 4 | Camphor | 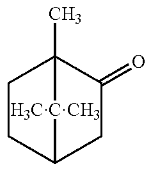 |
| 5 | Pinene | 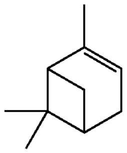 |
| 6 | Menthone | 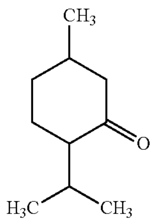 |

TABLE 3-continued
| T # | Compound name | Chemical structure |
| --- | --- | --- |
| 7 | Menthyl acetate | 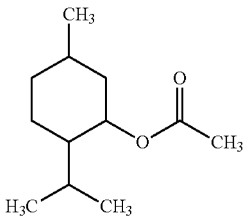 |
| 8 | Menthofuran | 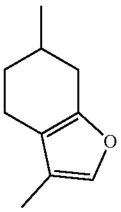 |
| 9 | Limonene | 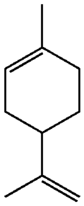 |
| 10 | Pulegone | 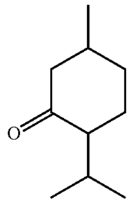 |
| 11 | alpha-phellandrene | 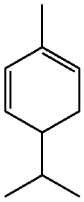 |
| 12 | beta-phellandrene | 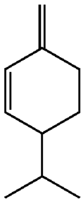 |
| 13 | Terpineol oxetane derivative (3,7-Dimethyl-1-oxaspiro[3.5]nonane) | 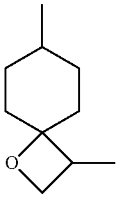 |

TABLE 3-continued

| T # | Compound name | Chemical structure |
|---|---|---|
| 14 | Piperitenone oxide | 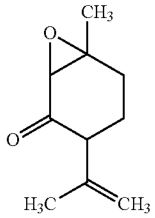 |
| 15 | Sabinene | 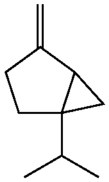 |
| 16 | Eugenol | 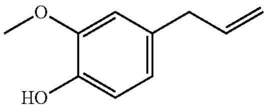 |

In an embodiment, the composition further comprises compounds selected from one or more of: Menthol, Eucalyptol, Terpineols (e.g. α, β, γ and 4-), Camphor, Pinene, Menthone, Menthyl acetate, Menthofuran, Limonene, Pulegone, alpha-phellandrene, beta-phellandrene, Terpineol oxetane derivative, Piperitenone oxide, Sabinene and Eugenol. In an embodiment, the second lip interacting component is selected from one or more of: menthol; eucalyptol, alpha-terpineol; camphor, pinene, sabinene or eugenol. In an embodiment, the second lip interacting component is selected from one or more of: menthol or eucalyptol. Menthol may for example be derived from menthol crystals or Menthol Liquid Essential Oil. Eucalyptol may for example be derived from Eucalyptus Essential Oil.

According to a specific embodiment of the invention, there is provided a composition comprising a sanshool compound, together with one or more of menthol and eucalyptol. In a further embodiment of the invention, there is provided a composition comprising a spilanthol compound, together with one or more of menthol and eucalyptol.

In an embodiment, the composition comprises one or more compounds defined in Tables 1 or 2, and/or components defined in the passages therebetween, together with one or more of menthol and eucalyptol. In an embodiment, the composition comprises an alpha-hydroxy sanshool compound, together with one or more of menthol and eucalyptol. In an embodiment, the composition further comprises one or more essential oils having a strong scent. In an embodiment, the sanshool compound is hydroxy-α-sanshool and the one or more essential oils are selected from thyme essential oil, pine essential oil and rosemary essential oil.

Herein disclosed, is a topical composition as described hereinabove formulated for application to the lips of an individual, as a lip balm, lip stick, lip gloss or lip salve. In an embodiment, the active component, first lip interacting component is present in a concentration of in excess of about 0.001, 0.01, 0.1, 0.5, 1, 2, 5 10, 15, 20, 30, 40, 50, 60, 75, 100, 150 and 200 grams per kilogram (g/kg) of the composition. Optionally, 10 to 60 g/kg, further optionally 20 to 40 g/kg and still further optionally about 25 to 30 g/kg of the lip interacting component or first lip interacting component. In embodiments where the active component, first lip interacting component is a sanshool or a combination of sanshools (such as any one or more of the compounds listed in Table 1), the active component is present in the composition in an concentration of in excess of about 0.001, 0.01, 0.1, 0.25, 0.5, 1.0, 2.0, 5.0, 10, 50, 100, 500 and 1000 mg/kg. In specific embodiments of the invention, the active component, first lip interacting component is a sanshool or a combination of sanshools (such as any one or more of the compounds listed in Table 1), the active component is present in the composition in an concentration of less than about 1000, 500, 100, 50, 10, 5.0, 2.0, 1.0, 0.5, 0.25, 0.1, 0.01, 0.001 mg/kg.

The component may be for example held in a liquid, semi-liquid or solid carrier medium. For example, 1 to 50% of the component, or a natural extract comprising the component, may be in a carrier oil, e.g. sunflower oil, rapeseed oil or olive oil. Other suitable carriers may include, but are not limited to, liquid paraffin, paraffin wax, microcrystalline wax, polybutene, polyisobutene, fatty acid alcohols (e.g. stearyl and oleyl alcohol, or octyldodecanol), glycerin, propylene glycol, beeswax, coconut oil, cocoa butter, lanolin, and shea butter.

In an embodiment, a second lip interacting component, when present in the composition, is menthol or eucalyptol, wherein the menthol and/or eucalyptol is present in a concentration of in excess of about 1, 5, 10, 25, 50, 100, 125, 150, 175, 200, 300, 400 and 500 grams per kilogram of the composition. Optionally, 50 to 300 g/kg, further optionally 100 to 200 g/kg and still further optionally about 130 to 160 g/kg of the second lip interacting component.

In an embodiment, a scent or flavour component such as a thyme essential oil, pine essential oil and/or rosemary essential oil, when present in the lip balm, lip salve or lip stick, is present in a concentration of in excess of about 0.1, 0.5, 1, 2, 5, 8, 10, 12, 15, 20, 30, 50 and 100 grams per kilogram of the composition. Optionally, 1 to 20 g/kg, further optionally 5 to 12 g/kg and still further optionally about 8 g/kg of the oil. In an embodiment, the balance of the composition, lip balm, lip salve, lip gloss or lip stick is made up of one or more of: emolument, surfactant, filler, preservative, colouring, perfume, flavouring etc; such ingredients for example including cacao butter, beeswax, coconut oil, almond oil, avocado oil, saffron oil, water, solvent, such that the composition has the physical and organoleptic properties making it suitable to formulate as a lip balm, lip salve, lip gloss or lip stick. In an embodiment, the ingredients are naturally sourced and organically sourced ingredients.

According to a specific a composition is provided, wherein the composition is a lip salve and comprises:

not less than 1% wt of a sanshool containing extract of Sichuan peppercorns, not less than 1% wt of a spilanthol containing extract of *Acmella oleracea* (e.g. spilanthes), with the balance made up of a liquid, semi-liquid or solid carrier medium as described above. Suitably, the composition may further comprise not less than 0.5% wt of menthol essential oil. The composition may also comprise additional scent and flavouring essential oils as described herein.

According to embodiments of the present invention any one of the compositions provided may be used to inhibit between meal snacking of a user. Likewise, any one of the compositions may be used in cosmetic or non-cosmetic methods for managing weight loss or weight gain, for example as part of a weight management regime, structured diet plan or to treat obesity or related bariatric illness. Hence according to an embodiment, there is provided a method of assisted weight loss, wherein the method comprises the application of a composition comprising one or more lip interacting components to the lips of a user between regular meals, the composition providing a noticeable sensory stimulation of the lips of the user.

According to embodiments of the present invention any one of the compositions provided may be used to inhibit smoking, vaping or any other form of illicit drug use. Likewise, any one of the compositions may be used in cosmetic or non-cosmetic methods for managing smoking or vaping addiction (e.g. cigarettes, cigars, pipes, e-cigarettes, vaping machines, shisha pipes etc.), the effects thereof, and/or to treat related illnesses. Cosmetic treatments to address the non-health related implications of smoking and vaping include the prevention of skin and tooth discoloration and premature dermal ageing associated with smoking and vaping, as well as reducing the odour associated with consumption of tobacco, marijuana or other volatiles having a strong and potentially unpleasant odour.

In an embodiment, the composition provides a sensory overload in the mouth area of the user. In an embodiment, the composition is formulated as a solid, gel or liquid composition. In an embodiment, the composition is formulated as a lip balm, lip salve or lip stick. In another embodiment, the composition is formulated as a mouth spray, lozenge, edible item, chewing gum, inhaler, nasal spray, nebulizer composition, patch, dermal patch, mucous membrane patch or gum guard. In an embodiment, the composition is formulated to provide a fast-drying film and may be painted on the surface of the lips, such as a lip gloss.

In a further embodiment of the invention the formulations may be used to deter chewing, sucking or biting of the hands or fingers, the composition comprising one or more active lip interacting components, the lip interacting components noticeably stimulating the lips or mouth area of the user. Without being bound by theory, the composition could be used to deter biting, sucking or chewing, e.g. by animals or children. For example, deterring children from chewing on their nails or sucking on their thumbs. Herein disclosed, is a use to deter chewing, sucking or biting, wherein the composition is defined hereinabove or in the claims.

The present invention will now be further described with reference to the following non-limiting examples.

EXAMPLES

Example 1—Lip Balm Formulation

TABLE 4

| Component | Amount (g) per kg of composition |
|---|---|
| Coconut Oil | 220 |
| Sichuan Peppercorn Oil | 210 |
| Cacao Butter | 170 |
| Menthol Crystals | 155 |
| Beeswax | 140 |
| Avocado Oil | 50 |
| Menthol Liquid Essential Oil | 18 |
| Eucalyptus Essential Oil | 10 |
| Rosemary Essential Oil | 9 |
| Thyme Essential Oil | 9 |
| Pine Essential Oil | 9 |

Without wishing to be restricted or bound by theory, it has been found that a heat and tingling/fizzing sensation generated in the lips by this formulation provides an effective distraction to aid/support a person wishing to avoid unwanted snacking. A cooling/numbing sensation is also provided by this embodiment and provides an additional source of snacking distraction. A combination of heat and tingling/fizzing sensation with a second sensation like a cooling/numbing sensation may provide a greater distraction from snacking than each sensation alone thereby acting synergistically. Without wishing to be restricted or bound by theory, it is believed that these contrasting sensations help to provide a sensory overload in the mouth area, helping to further distract the user from the snacking urge.

Example 2—Formulation

TABLE 5

| Component | Amount (g) per kg of composition |
|---|---|
| Coconut Oil | 220 |
| Infused Chilli Extract | 210 |
| Virgin Olive Oil | |
| Cacao Butter | 170 |
| Menthol Crystals | 155 |
| Beeswax | 140 |
| Avocado Oil | 50 |
| Menthol Liquid Essential Oil | 18 |
| Eucalyptus Essential Oil | 10 |
| Limonene Essential Oil | 9 |
| Citronella Essential Oil | 9 |
| Orange Oil | 9 |

Example 3—Formulation

TABLE 6

| Component | Amount (g) per kg of composition |
|---|---|
| Coconut Oil | 220 |
| Infused Chilli Extract | 210 |
| Virgin Olive Oil | |

TABLE 6-continued

| Component | Amount (g) per kg of composition |
| --- | --- |
| Cacao Butter | 170 |
| Menthol Crystals | 155 |
| Beeswax | 140 |
| Avocado Oil | 50 |
| Menthol Liquid Essential Oil | 18 |
| Eucalyptus Essential Oil | 10 |
| Coffee Fragrance Oil | 9 |
| Freshly Cut Grass Fragrance Oil | 9 |
| Vanilla Extract | 9 |

Example 4—Formulation

TABLE 7

| Component | Amount (g) per kg of composition |
| --- | --- |
| Coconut Oil | 220 |
| Sichuan Peppercorn Oil | 210 |
| Cacao Butter | 170 |
| Menthol Crystals | 155 |
| Beeswax | 140 |
| Avocado Oil | 50 |
| Marmite ™ (as formulated Jan. 1, 2019) | 27 |
| Menthol Liquid Essential Oil | 18 |
| Eucalyptus Essential Oil | 10 |

Example 5—Formulation

TABLE 8

| Component | Amount (g) per kg of composition |
| --- | --- |
| Coconut Oil | 220 |
| Sichuan Peppercorn Oil | 110 |
| Infused Chilli Extra Virgin Olive Oil | 110 |
| Cacao Butter | 170 |
| Menthol Crystals | 155 |
| Beeswax | 140 |
| Avocado Oil | 50 |
| Menthol Liquid Essential Oil | 18 |
| Eucalyptus Essential Oil | 10 |
| Rosemary Essential Oil | 9 |
| Thyme Essential Oil | 9 |
| Pine Essential Oil | 9 |

Example 6—Formulation

TABLE 9

| Component | Amount (g) per kg of composition |
| --- | --- |
| Szechuan Peppercorn Oil (Rapeseed Oil 88%, Szechuan peppercorn 12%) | 245 |
| Coconut Oil | 165 |
| Menthol Crystals | 138 |
| Cacao Butter | 120 |
| Beeswax | 100 |
| Almond Oil | 80 |

TABLE 9-continued

| Component | Amount (g) per kg of composition |
| --- | --- |
| Menthol Liquid Essential Oil | 16 |
| Eucalyptus Essential Oil | 8 |
| Rosemary Essential Oil | 8 |
| Thyme Essential Oil | 8 |
| Pine Essential Oil | 8 |

The lip balm of Example 1 took the form of a gel-like substance and was placed in a squeezable tube.

Example 7—Testing of the Composition of Example 1

A group of 35 respondents completed the test. The respondents were between the ages of 18 to 65; 6 were male and 29 were female. The respondents were given 2 tubes of lip balm, each tube containing a formulation as defined in Example 1. Each respondent completed one control week (i.e. not using the Example 1 composition) and a test week using the Example 1 composition. The order of the two weeks was balanced across the group.

During the test week the respondents used the lip balms whenever they felt the urge to snack. At the end of each day (control and test week) respondents completed a questionnaire. The daily questionnaire asked about how often they felt the urge to snack, how often they resisted the urge and how long the effect lasted.

Results

| | Control week | Test week |
| --- | --- | --- |
| Average times the user had an urge to snack per day: | 3.3 | 3.2 |
| Average times urge to snack was resisted per day: | 1.3 | 2.3 |
| Average % times urge to snack was resisted per day: | 39% | 72% |

Conclusion—by using the invention, the ability of the user to resist snacking increased from 39% to 72%, meaning the user moved from a default position of 'likely to snack', to a position of 'unlikely to snack' (i.e. the ability to resist the urge to snack was nearly doubled).

Questionnaire Results

The questionnaire revealed that 83% (i.e. 29 of 35) of the respondents believed the product helped to reduced instances of snacking.

Active Properties

Of the 83% of the respondents that believed the product helped to reduce the instances of snacking, the questionnaire revealed that this was principally attributed to:

| | | |
| --- | --- | --- |
| Sensation imbued in the lips (e.g. tingling): | 59% | (i.e. 17 of 29) |
| Flavour: | 17% | (i.e. 5 of 29) |
| Aroma: | 14% | (i.e. 4 of 29) |
| Action of applying the lip balm: | 10% | (i.e. 3 of 29) |
| Other (e.g. texture): | 0% | (i.e. 0 of 29) |

Conclusion—the respondents believed the primary mode of action originated from the sensation generated in the lips.

This choice was selected over three times more than the next highest option selected. The flavour, and then aroma, were the next most highly chosen options. A few respondents attributed the mode of action to putting the composition on.

Window of Activity

The questionnaire revealed that the period of time (i.e. 7 days of responses) in which the 35 respondents believe the action of Example 1 was noticeable:

| | | |
|---|---|---|
| 5-10 minutes: | 11% | (i.e. 28 of 245 responses) |
| 10-15 minutes: | 17% | (i.e. 14 of 245 responses) |
| 15-30 minutes: | 40% | (i.e. 97 of 245 responses) |
| 30-60 minutes: | 23% | (i.e. 57 of 245 responses) |
| 60+ minutes: | 9% | (i.e. 22 of 245 responses) |

Conclusion—the respondents could sense the action of the composition of Example 1 for at least 5 minutes and up to at least 60 minutes. The average time of activity (assuming that 60+ minutes is exactly 60 minutes) was about 27 minutes.

Example 8—Testing of a Composition Comprising Sanshool and Spilanthol for Dietary Management in Overweight or Obese Individuals A trial of 107 respondents completed this test, with a further 24 respondents using a placebo product that omitted the Sichuan peppercorn oil, menthol, essential oil and spilanthes components (with the balance made up with non-active carrier). The respondents were all adults and were divided 85% female and 15% male. The respondents all had a BMI in excess of 25, with 50% having a BMI in excess of 30 indicating that they were clinically obese. All of the respondents indicated that prior to the trial they habitually consumed at least three food items (i.e. snacks) between and in addition to established mealtimes.

Example 8 Active Formulation

TABLE 10

| Component | Amount (g) per kg of composition |
|---|---|
| Coconut Oil | 220 |
| Sichuan Peppercorn Oil (Rapeseed oil 88%, Sichuan peppercorn 12%) | 240 |
| Cacao Butter | 180 |
| Menthol Crystals | 135 |
| Beeswax | 140 |
| Avocado Oil | 35 |
| Menthol Liquid Essential Oil | 17 |
| Eucalyptus Essential Oil | 8 |
| Rosemary Essential Oil | 5 |
| Spilanthes | 20 |

The respondents were each given 2 tubes of lip salve either active formulation or placebo depending upon which group they were in. Each respondent completed one baseline week of testing and a test week. The order of the two weeks was balanced. During the testing week, respondents used the lip salve whenever they felt the urge to snack between standard mealtimes of breakfast, lunch or evening meal. At the end of each day (baseline and test week) the respondents completed a questionnaire. The daily questionnaire asked about how often they felt the urge to snack, how often they resisted the urge and (in the test week only) how long the effect of the lip salve lasted. At the end of the test week, respondents were asked about the effectiveness of the lip salve.

Results

TABLE 11

| | Active Group baseline week | Active Group test week | Placebo Group baseline week | Placebo Group test week |
|---|---|---|---|---|
| Times resisted snacking as a % of urges to snack | 33% | 69% | 30% | 55% |

Both groups reported that they were able to resist the urge to consume food between established mealtimes only around a third of the time during the baseline week. During the test weeks the ability to resist the urge to snack increased for both groups using the active and placebo formulations. However, in those using the active formulation this increased significantly to 69% of the time ($p<0.05$). Thus, the active formulation more than doubled the respondents' ability to resist the urge to snack. The results are further shown in FIG. 1 which shows the comparisons of the frequency of daily urges to snack alongside the ability to resist the urge in all groups tested.

When questioned at the end of the trial 88% of the respondents in the active group expressed the opinion that the product helped them to resist the urge to snack ($p<0.05$). This fell to 67% in the placebo group ($p<0.05$).

Within the active group for those that responded that product helped them to resist the urge to snack more than half attributed this to the sensation elicited by the formulation when applied to their lips. For around two thirds of respondents this sensation persisted for more than 15 minutes and in many cases up to one hour post-application, thereby effectively covering the time period in which the urge to snack occurred.

Conclusion—the formulations show a statistically significant effect on controlling habitual urges to consume food outside of regular mealtimes in clinically overweight and obese individuals when compared to a placebo formulation.

Example 9—Testing of a Composition Comprising Sanshool and Spilanthol for Promoting Cessation of Smoking or Vaping A total of 27 individuals took part in a smoking cessation trial using the same active and placebo formulations of Example 8. 14 respondents completed the test using the active product, while a further 13 respondents completed the test using the placebo product. Each respondent completed four baseline days and four test days. The order of these was balanced. During the test days, respondents used the lip salve whenever they felt the urge to smoke. At the end of each day (baseline and test days) respondents completed a questionnaire. The daily questionnaire asked about how often they felt the urge to smoke, how often they resisted the urge and (on the test days only) how long the effect of the lip salve lasted.

The respondents were all adults between the ages of 18 and 65 broken down into 48% female and 52% male. The majority (93%) of the respondents were moderate smokers consuming between 5 and 20 cigarettes per day. The remaining respondents were classed as heavy smokers consuming in excess of 20 cigarettes. All respondents indicated that they were actively trying to quit smoking and were using a range of smoking cessation aids already. Respondents continued to use their smoking cessation aids throughout the study including during the baseline period.

Results

TABLE 12

| | Active Group baseline week | Active Group test week | Placebo Group baseline week | Placebo Group test week |
|---|---|---|---|---|
| Times resisted smoking as a % of urges to smoke | 31% | 42% | 23% | 34% |

The results demonstrate that there was an increase in the ability to resist of the urge to smoke for respondents using the active formulation compared to baseline and also placebo ($p<0.05$). This is more evident if the baseline groups are pooled as shown in Table 13.

TABLE 13

| | Baseline groups combined | Active Group test week | Placebo Group test week |
|---|---|---|---|
| Times resisted smoking as a % of urges to smoke | 27% | 42% | 34% |

For those respondents using the active formulation and who felt is helped them to resist the urge to smoke, most attributed the effect to the sensation the formulation elicited on their lips following application.

Conclusion—the formulations demonstrate a clear positive effect on controlling habitual urges to smoke in moderate to heavy smokers who are attempting to quit when compared to baseline and a placebo formulation. The formulations of the invention were successful in increasing the effectiveness of the urge to resist smoking above the smoking cessation aids already being used by the respondents. This suggests the formulations are suitable for use in conjunction with a range of other products aimed at treating smoking and vaping.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

The invention claimed is:

1. A method for reducing a habitual urge to consume food between regular mealtimes in an individual subject, the method comprising applying a composition to a dermal layer of the lips of the individual subject when the individual subject senses the urge to consume food, and wherein;

the composition comprises at least one sanshool, the composition comprises an amount of the at least one sanshool sufficient to induce a somatosensory sensation in the dermal layer of the lips, and the composition is formulated as at least one of a lip balm, a lip salve, a lip gloss or a lip stick.

2. The method of claim 1, wherein the method is a method for managed weight loss or weight maintenance.

3. The method of claim 1, wherein the habitual urge is a habitual urge to consume food between regular mealtimes and the method is for weight maintenance.

4. The method of claim 1, wherein the sanshool is selected from one or more of the group consisting of:

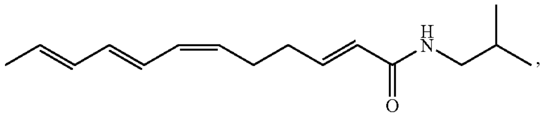

α-Sanshool

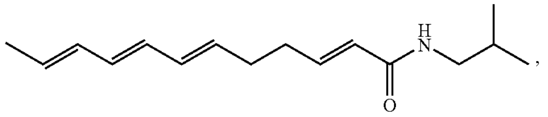

β-Sanshool

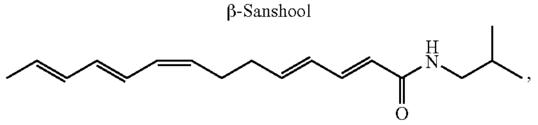

γ-Sanshool

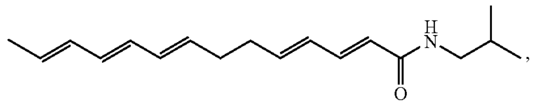

δ-Sanshool

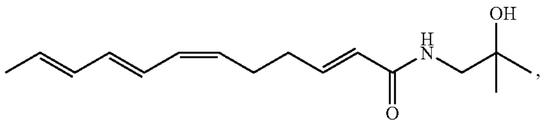

Hydroxy-α-sanshool

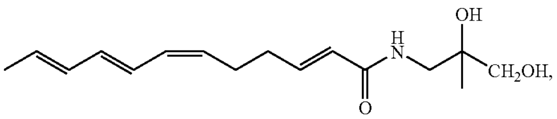

Dihydroxy-α-sanshool

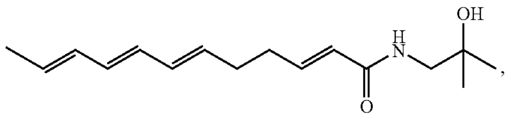

Hydroxy-β-sanshool

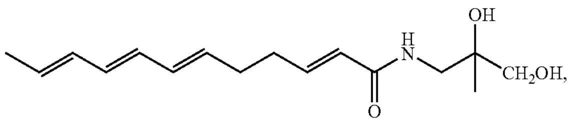

Dihydroxy-β-sanshool

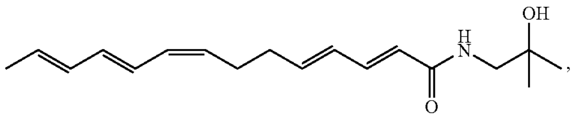

Hydroxy-γ-sanshool

-continued

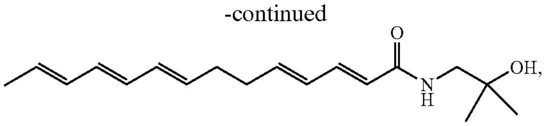

Hydroxy-γ-isosanshool

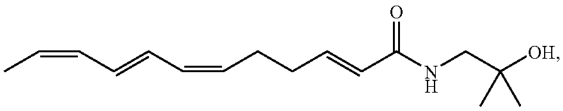

Hydroxy-ε-sanshool

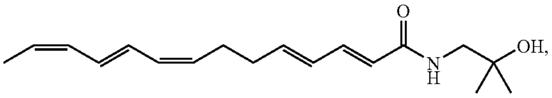

Hydroxy-ς-sanshool

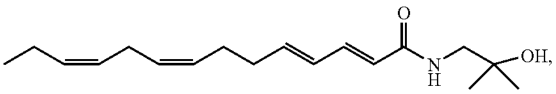

Bungeanool

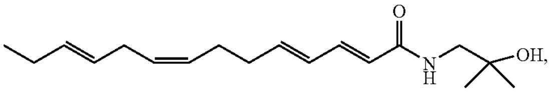

Isobungeanool

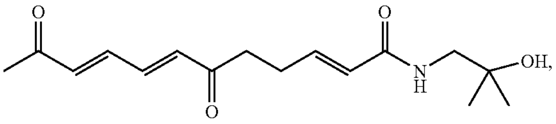

(2E,7E,9E)-N-(2-hydroxy-2-methylpropyl)-6,11-dioxo-2,7,9-dodecatrienamide

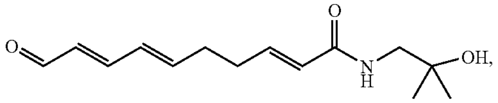 and (2E,6E,8E)-N-(2-hydroxy-2-methylpropyl)-10-oxo-2,6,8-decatrienamide

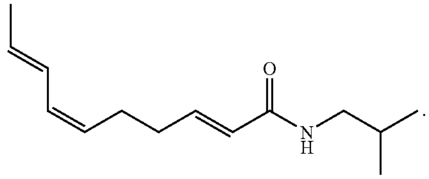

Spilanthol

5. The method of claim 4, wherein the sanshool is hydroxy-α-sanshool.

6. The method of claim 4 wherein the sanshool is spilanthol.

7. The method of claim 1, wherein the composition comprises at least a first sanshool and at least a second sanshool.

8. The method of claim 7, wherein the first sanshool is hydroxy-α-sanshool and the second sanshool is spilanthol.

9. The method of claim 1, wherein the composition further comprises an essential oil selected from one or more of the group consisting of: thyme essential oil; rosemary essential oil; pine essential oil; lavender essential oil; and a citrus essential oil.

10. The method of claim 1, wherein the composition further comprises a capsaicinoid, such as capsaicin, or a related compound, or a pungent component extracted or extractable from chilli peppers.

11. The method of claim 1, wherein the composition further comprises a compound selected from one or more of the group consisting of: menthol; eucalyptol, alpha-terpineol; camphor, pinene, eugenol; and sabinene.

12. The method of claim 1, wherein the composition further comprises a dysgeusic component, which alters a perception of taste in the individual subject.

13. The method of claim 1, wherein the somatosensory sensation induces a perception of vibration in the dermal layer of the lips.

14. The method of claim 1, wherein the somatosensory sensation induced in the dermal layer of the lips by the composition is perceived by the individual subject for a period of time in excess of about five minutes.

15. The method of claim 1, wherein the composition induces a paresthesia sensation in the dermal layer of the lips.

16. The method of claim 15, wherein the paresthesia sensation induced in the dermal layer of the lips by the composition is perceived by the individual subject for a period of time in excess of about five minutes.

17. The method of claim 1, wherein the at least one sanshool is held in a liquid, semi-liquid or solid carrier medium.

18. The method of claim 17, wherein carrier medium comprises one of more of the group consisting of: liquid paraffin; paraffin wax; microcrystalline wax; polybutene; polyisobutene; fatty acid alcohols; glycerin; propylene glycol; beeswax; coconut oil; cocoa butter; lanolin; and shea butter.

19. The method of claim 1, wherein the composition is a lip salve and comprises:

not less than 1% wt of a sanshool containing extract of Sichuan peppercorns; and not less than 1% wt of a spilanthol containing extract of *Acmella oleracea,* with the balance made up of a liquid, semi-liquid or solid carrier medium.

20. The method of claim 1, wherein the somatosensory sensation induced in the dermal layer of the lips by the composition is perceived by the individual subject for a period of time in excess of about forty minutes.

21. The method of claim 15, wherein the paresthesia sensation induced in the dermal layer of the lips by the composition is perceived by the individual subject for a period of time in excess of about forty minutes.

* * * * *